(12) United States Patent
Scheffler

(10) Patent No.: US 7,482,383 B2
(45) Date of Patent: Jan. 27, 2009

(54) EMULSION CONTAINING A PLANT EXTRACT, METHOD FOR PRODUCING SAID EMULSION AND FOR OBTAINING SAID PLANT EXTRACT

(75) Inventor: Armin Scheffler, Niefern-Öschelbronn (DE)

(73) Assignee: Birken GmbH, Niefern-Oschelbronn (DE)

( * ) Notice: Subject to any disclaimer, the term of this patent is extended or adjusted under 35 U.S.C. 154(b) by 0 days.

(21) Appl. No.: 11/748,304

(22) Filed: May 14, 2007

(65) Prior Publication Data

US 2007/0231418 A1    Oct. 4, 2007

Related U.S. Application Data

(63) Continuation of application No. 10/239,929, filed as application No. PCT/EP01/03417 on Mar. 26, 2001, now abandoned.

(30) Foreign Application Priority Data

Mar. 28, 2000 (DE) ............... 100 15 353
Nov. 16, 2000 (DE) ............... 100 56 902

(51) Int. Cl.
*B01F 3/08* (2006.01)
*B01F 17/00* (2006.01)
*A61K 31/01* (2006.01)

(52) U.S. Cl. ............ 516/53; 514/762; 516/9; 516/905

(58) Field of Classification Search .......... 516/9, 516/53, 905; 514/762
See application file for complete search history.

(56) References Cited

U.S. PATENT DOCUMENTS

| | | | |
|---|---|---|---|
| 2,764,620 A | | 9/1956 | Findlay |
| 4,044,031 A | | 8/1977 | Johansson et al. |
| 4,265,824 A | | 5/1981 | Koskenniska et al. |
| 4,732,708 A | | 3/1988 | Ekman et al. |
| 5,166,176 A | | 11/1992 | Obagi et al. |
| 5,466,452 A | | 11/1995 | Whittle |
| 5,647,976 A | | 7/1997 | Rothe et al. |
| 5,660,727 A | | 8/1997 | Gleave et al. |
| 5,753,493 A | * | 5/1998 | Wiersma ............ 435/261 |
| 5,780,196 A | | 7/1998 | Fujiwara et al. |
| 5,785,856 A | | 7/1998 | Gleave et al. |
| 5,843,311 A | | 12/1998 | Richter et al. |
| 5,882,916 A | * | 3/1999 | Wiersma ............ 435/261 |
| 6,008,246 A | * | 12/1999 | Ito et al. ............ 514/458 |
| 6,124,362 A | * | 9/2000 | Bradbury et al. ........ 514/569 |
| 6,175,035 B1 | | 1/2001 | Draeger et al. |
| 6,264,998 B1 | | 7/2001 | Ramadoss et al. |
| 6,280,778 B1 | | 8/2001 | Gaudet et al. |
| 6,342,208 B1 | | 1/2002 | Hyldgaard et al. |
| 6,392,070 B1 | * | 5/2002 | Krasutsky et al. ........ 552/545 |
| 6,682,763 B2 | | 1/2004 | Kuno et al. |

FOREIGN PATENT DOCUMENTS

| CA | 2385139 A1 | 4/2001 |
|---|---|---|
| DE | 43 18 280.1 A1 | 12/1993 |
| DE | 195 44 905.3 A1 | 6/1997 |

OTHER PUBLICATIONS

Lowitz, M., "On a novel, almost benzoin-like, substance from birches," Chemische Analysen, Hrsg. Crell, L., 2: 312.

Hausmann, U., "On betulin, (an excerpt from the author's PHD thesis, Göttingen 1876)" Annalen der Chemis, 182: 368.

Hayek, E.W. et al., , A Bicentennial of Betulin, Phytochemistry, 28(9): 2229-2242, (1989).

Ekman, R., "The Suberin Monomers and Triterpenoids from the Outer Bark of Betula verrucosa Ehrh.," Holzforschung, 37: 205-211, (1983a).

Ekman, R., "Lipophilic Extractives of the Inner Bark of Birch, Betula verrucosa Ehrh.," Finn. Chem. Letters, p. 162, (1983b).

Jääskeläinen, P., "Betulinol and its utilisation," Paperi ja Puu—Papper och Trä 10: 599-603, (1981).

Wheeler, J., Pharm. J., The Production of Betulin by Sublimation, 494, Ref. Chem. Centr. 1900 I: 353, (1899).

(Continued)

*Primary Examiner*—Timothy J Kugel
(74) *Attorney, Agent, or Firm*—Akerman Senterfitt; Gregory A. Nelson; Peter A. Chiabotti

(57) ABSTRACT

The invention provides a continuous process for obtaining triterpenes from plants and/or their components. The process can include continuously washing at least one of plant and plant parts in counter-current at 20° C. to 70° C. with a solvent in which the triterpenes are not soluble or only slightly soluble and continuously extracting triterpenes from the washed plant part or parts with a solvent under an increased pressure and an elevated temperature relative to the washing pressure and temperature in counter-current to form a triterpene containing solution where the plant parts are conveyed in counter-current to the solvent flow, on the basis of their different density in a pressure-tight and heatable tube and are discharged at an end of the tube opposite to the solvent discharge. The process can also include the steps of continuously cooling and depressurizing the triterpene containing solution, where triterpene crystallizes out of the solvent, filtering the triterpene crystals from the solvent at room temperature and washing the triterpene crystals in fresh solvent.

18 Claims, 1 Drawing Sheet

OTHER PUBLICATIONS

Hansel, R. et al., (Hrsg.), Drug A-D, Springer Publishing House, Chapter Betula, 502-511, (1994).

Chen Sun, J. et al., "Anti-AIDS Agents, 32, Synthesis and anti-HIV activity of Betulin derivates," Bioorganic & Medical Chemistry Letters 8: 1267-1272, (1998).

Evers, M. et al., Betulinic acid derivates: a new class of human immunodeficiency virus type 1, specific inhibitors with a new mode of action, J. Med. Chem. 39:1056-68 (1996).

Carmen Recio, M., et al., "Investigations on the steroidal anti-inflammatory activity of triterpenoids from Diospyros leucomelas," Planta Med. 61: 9-12, (1995).

Yasukawa, K., et al., "Sterol and triterpene derivates from plants Inhibit the Effects of Tumor Promoter . . . ," Oncogene 48: 72-76, (1991).

Ukkonen, K., et al., "Birch Bark Extractives," Kemia-Kemi 5: 217-220, (1979).

Eckermann, C., et al., "Comparison of solvents for extraction and crystallization of betulinol from birch bark waste," Paperi ja Puu—Papper och Tra 3: 100-106, (1985).

O'Connell, M.M. et al., "Betulin and Lupeol in Bark from four white-barked birches," Phytochemistry 7: 2175-2176, (1988).

Hua, Y. et al., "Triterpenes From the Outer Bark of Betula Nigra," Journal of Wood Chemistry and Technology 11(4): 503-516, (1991).

Pasich, J., Triterpenoid emulsifiers of plant origin. V. Emulsifying properties of Betulin and certain of its esters. Farm. Polska 21, Nr. 17-18: 661-666, (1965).

Nowak, G. A., Cosmetic and Medicinal Properties of the Birch, Amer. Perfumer Cosmet., 81: 37, (1966).

* cited by examiner

EMULSION CONTAINING A PLANT EXTRACT, METHOD FOR PRODUCING SAID EMULSION AND FOR OBTAINING SAID PLANT EXTRACT

CROSS REFERENCE TO RELATED APPLLICATIONS

This application is a continuation application claiming priority to currently pending U.S. patent application Ser. No. 10/239,929 filed on Sep. 26, 2002, with the title EMULSION CONTAINING A PLANT EXTRACT, METHOD FOR PRODUCING SAID EMULSION AND FOR OBTAINING SAID PLANT EXTRACT, which was a 371 National Stage Entry of PCT/EP01/03417, filed on Mar. 26, 2001, the entirety of which are hereby incorporated by reference.

The present invention concerns a process for obtaining triterpenes and/or their components, as well as an emulsion, of which the aqueous and fatty phases are emulsified by a plant extract, wherein the plant extract contains at least one triterpene and/or a triterpene divertive, and the emulsion further contains, at least, one oil and/or fat and water. Besides this, the present invention concerns a process for producing the emulsion, as well as the use of the triterpenes for production of cosmetics and pharmaceuticals.

Natural ingredients, fragrances or flavors, and active substances, have for a long time, been isolated, using various extraction techniques, from whole plants and their parts, such as leaves, roots, fruits, or bark. As one of the first natural substances, betulin (birch camphor), the substance which imparts to birch bark its white color, was extracted from plant material in the year 1788 (Lowitz, M., Chemische Analysen, Hrsg. Crell, L., Vol. 2, page 312). Subsequent to this first isolation there followed scientific studies, including elementary analysis of betulin, which were published by U. Hausmann 1876 (Hausmann, U., Annalen der Chemis, 182, page 368).

Betulin containing plants are widely distributed in the plant kingdom. They belong primarily to the Hamamelididae (angiosperm plants), where in one single species in the order fagales (birch relatives), and more particularly, in the family of the betulaceen (birches), the content of betulin accumulates in the outer bark (review article: Hayek, E. W. et al., (1989), A Bicentennial of Betulin, Phytochemistry, 28(9), pages 2229-2242). The white part of the birch bark, in particular, the species *betula pedula, betula verrucosa*, and *betula papyfera* can contain more than 30% betulin. More precise research was published by Rainer Ekman in the year 1983, according to which 21-40% triterpene, or 16.7-34% betulin, were extracted from the dry outer bark of *betula verrucosa* (Ekman, R. (1983a), Holzforschung, 37, page 205-211). The inner bark, in comparison, contained only traces of triterpenes, in the realm of approximately 0.37-0.43% (Eckman, R. (1983b), Finn. Chem. Letters, page 162).

Betulin is a pentacyclic triterpene with a lupan skeleton, which is also referred to as betulinol, trochoton, birch camphor and (coryli) resinol. The characterizing feature of the lupan group is a ring with five carbon atoms within the pentacyclic system, which contains an α-isopentyl group in the position C-19. Betulin is further characterized by a high thermal stability. Its melting point lies between 250 and 260° C., wherein even high values are obtained after sublimation of the re-crystallized product. Its molecular weight is 442.7, and it is only soluble in pyridine and tetrahydrofuran. However, it is only slightly soluble in dichloromethane, chloroform, and cold organic solvents, wherein its solubility significantly increases with increasing temperature. In water and cold petroleum ether [hydrocarbon with 5 to 8 C-atoms ($C_5$-$C_8$ CH)] betulin is practically insoluble. Besides this, kinetic research has shown low reactivity of the hydroxy group of betulin (review article: Jääskeläinen, P. (1981), Paperi ja Puu-Papper och Trä 10, pages 599-603).

Already in the year 1899, J. Wheeler demonstrated the antiseptic characteristics of betulin, it is thus used for sterilization of bandages and adhesive medical plaster (Wheeler, J. 1899), Pharm. J., The Production of Betulin by Sublimation, 494, Ref. Chem. Centr. 1900 I, page 353). In natural medicine and folk remedies, products from cooking birch bark were and are still employed, wherein, only the inner part is used, which contains only residue of the white birch bark. Due to its low solubility, it most likely contains no betulin, since the content of betulin in the inner bark is less than 0.5%, and betulin is insoluble in water or water-alcohol mixtures (up to 60% alcohol) (Ekman, R. (1983b), supra).

The, thus, obtained product of boiling is used for treatment of hot flashes, water craving, gout, and for skin diseases, as well as a tincture for bandages for abscesses. Further, birch bark is used for production of birch bark oil, which has also been used for treatment of rheumatism and as aroma therapy (Hansel, R. et al., (Hrsg.), (1994), Drug A-D, Springer Publishing House, Chapter Betula, pages 502-511; Hyek, E. W. supra). Besides this, the use of birch extracts as bath salts for treatment, particularly, for sweaty feet, as well as additives to shampoos, as a hair care agent is known (Nowak, G. A., (1966), Cosmetic and Medicinal Properties of the Birch, Amer. Perfumer Cosmet., 81, page 37). Here, however, only aqueous extracts from birch leaves have been employed, which contain practically no betulin.

Newer research suggests a medicinal effect of betulin and betulin derivatives. In animal tests betulinic acid inhibited the replication of retroviruses, in particular the human immune deficiency virus (HIV1). The published bacteriostatic and bactericidal effect of betulin against intestinal *Escherichia coli, Salmonella typhi, Shigella flexneri*, and *Staphylococcus aureus* suggest a broader medicinal application (Chen Sun, J. et al., (1998), Anti-AIDS Agents, 32, Synthesis and anti-HIV activity of Betulin derivates, Bioorganic & Medical Chemistry Letters 8, pages 1267-1272; Evers, M. et al.(1996), Betulinic acid derivates: a new class of human immunodeficiency virus type 1, specific inhibitors with a new mode of action, J. Med. Chem. 39, pages 1056-1068; Hayek, E. W. et al., supra). Further, an anti-inflammatory, cortisone like effect as well as cytostatic effect upon use in vitro against various tumor cell lines of betulin and betulin derivatives has been shown (Carmen Recio, M., et al. (1995), Investigations on the steroidal anti-inflammatory activity of triterpenoids from *Diospyros leucomelas*, Planta Med. 61, pages 9-12); Yasukawa, K., et al. (1991), Sterol and triterpene derivates from plants ( . . . ), Oncogene 48, pages 72-76).

For obtaining betulin from birch bark, in particular, from birch cork, one could consider using, besides sublimation (Lowitz, M., supra), above all extraction in broiling solvents. As solvent there are employed mainly alcohol and chlorinated hydrocarbons (Ukkonen, K. and Era, V. (1979), Kemia-Kemi 5, pages 217-220; Ekman, R. (1983a), supra; Eckermann, C. and Ekman, R. (1985), Paperi ja Puu—Papper och Tra 3, pages 100-106; O'Connell, M. M. et al. (1988), Phytochemistry 7, pages 2175-2176; Hua, Y. et al. (1991), Journal of Wood Chemistry and Technology 11(4), pages 503-516).

The disadvantage of the sublimation technique is the fact that the content is obtained only with very low yield, which necessitates the use of large amounts of starting materials. Besides this, a particular disadvantage of the sublimation technique is the simultaneous occurrence of tar-like decomposition products from other cork/bark components, which necessitates multiple re-sublimation or re-crystallization. With the use of the extraction method, it is particularly disadvantageous that betulin is relatively poorly soluble in the mentioned solvents, and the extraction can only be carried out with high investment in time. Here, also multiple re-crystallizations are necessary. The best results are obtained with higher boiling hydrocarbons (Eckermann, C. and Ekman, R. (1985), supra). These are, however, particularly disadvantageous for use in cosmetics and medicines due to the unavoidable residual solvents in the product.

Solvents in which betulin is highly soluble, such as—for example, pyridine and tetrohydrofuran, are generally considered to be toxins. They are dismissed on the basis of their health risk and their not insubstantial handling risks during extraction. A further disadvantage of the mentioned solvents is that substantial amounts of brown, undesired substances are dissolved at the same time, of which the later separation is extremely complex, costly, and uneconomical. Accordingly, until today, there is no efficient process for obtaining betulin from birch cork, whereby betulin can be produced in large amounts, with a high degree of purity and without using strong hazardous solvents.

In the state of the art, further processes are known for extraction of lipophilic natural substances using high pressure and high temperature. For example, in U.S. Pat. No. 5,843,311 a process is described for isolation of organic materials using organic solvents. With the aid of this analytic process, which is used on a small scale, samples can be tested for contaminants, impurities, or additives. This analytic process is used primarily for monitoring in the nutrition and health agent industry, in the pharmaceutical industry and in the analysis of ground samples. A disadvantage of this process is its limitation to the small analytical scale.

In U.S. Pat. No. 5,647,976 a reaction vessel is described, which can be employed for extraction of contents with solvents with high pressure and elevated temperature. This reaction vessel is characterized by a lock, which makes it possible to introduce solvents in the reaction vessel and to remove them therefrom, without having to disturb the lock. In this manner, contamination of the solvent is effectively prevented. In addition, the reaction vessel is simple to operate, so that it can be operated even by untrained personnel. U.S. Pat. No. 5,647,976 essentially describes the mentioned reaction vessel, however, it gives no direction as to how to carry out an extraction process. Besides this, it contains no indication regarding the quality and purity of the contents, which have been isolated in the reaction vessel. U.S. Pat. No. 5,660,727 discloses the use of the reaction vessel from U.S. Pat. No. 5,647,976 in an automatic rotation unit, which enables the simultaneous analysis of multiple samples. The volume of each reaction vessel, which can be introduced into the reaction unit lies between 10 and 30 ml. Thus, these devices find application in the analytic realm, and they are not suitable for employment in a large-scale framework.

In U.S. Pat. No. 5,785,856, which is a divisional of U.S. Pat. No. 5,660,727, there is described, besides the rotation device, also a process for extraction of components using solvents. The process is carried out under increased pressure and elevated temperature. For this, the reaction vessel is filled with the sample material to be analyzed, and the rotation unit is activated and automatically has solvent added to it. Subsequently the pressure and the temperature are increased to predetermined values. After successful extraction, the solvent is diverted to a receptacle container. The reaction vessel, inclusive of the supply and removal lines, can be rinsed with an inert gas, such as, for example, nitrogen for cleaning. A disadvantage of the process is, in particular, that it may be suitable for extracting soluble substances in an analytic sample. However, is not or is only poorly suitable for preparative production and yielding of components in greater amounts and purity, since it is precisely in such processes that contamination of the sample leads to defects in the degree of purity of the extracted components. Further, the process as described in U.S. Pat. No. 5,785,856 as conceived is limited to the analytical realm. The document provides no indication regarding obtainable degrees of purity, and the possibility for scaling up to industrial scale.

All processes described in the state of the art work discontinuously, that is, a predetermined amount is respectively extracted in a vessel to be filled and subsequently emptied. Until now, no continuous process has been made available, for continuously supplying plant materials and fresh solvent, extracting in a counter-current process, and simultaneously withdrawing the extract-saturated solvent, as well the completely extracted plant material.

Besides this, in the state of the art, various attempts have already been undertaken to modify the surface or scalp active characteristics of betulin, in order to produce technically useful products. So, for example, Pasich already carried out experiments in the 60's with betulin and its esters, such as the succianates, phthalates, and tetrachlorophthalates, as emulsifiers for white vaseline, whale oil, and peanut oil, and came to the conclusion that betulin, with respect to its emulsification properties, that its ability to connect aqueous and oily components with each other, was comparable with known technical or industrial emulsifiers. His betulin containing emulsifiers were, however, less stable. He employed re-crystallized betulin and achieved no satisfactory stability of the emulsions. Preferred were the phthalate and tetrachlorophthalate, which were produced with the objective of better water solubility. Oily layers separated out of the emulsions after a short time, which indicated its insufficient stability. Besides this, anti-microbial effective preservatives were added to the described emulsifiers, whereby primarily benzoic acid derivatives were employed (Pasich, J., 1965), Triterpenoid emulsifiers of plant origin. V. Emulsifying properties of Betulin and certain of its esters. Farm. Polska 21, Nr. 17-18, pages 661-666).

It is, however, precisely the addition of preservatives, which for their part can induce allergenic and toxic effects, which frequently destroy the positive therapeutic effect of the betulin, particularly on damaged skin, so that the preparations of betulin containing emulsions described in the literature cannot be used, or be used only to a limited extent, in modern skin care.

These disadvantages in the state of the art have resulted in no mentionable technical preparation, use, or employment of the triterpenes contained in birch cork. In particular, the betulin contained therein in large amounts, despite the large amounts of birch bark available today as waste product in wood harvesting.

The amounts of presently non-utilized betulin are enormous. Even considering only one single pulp factory in Finland (UPM Kymmene, Lappeenranta, Finland) an extractable amount of approximately 4,000 to 5,000 tons of betulin per year are incinerated as waste. In Sweden, Finland, Russia, and Canada, a large number of pulp factories of this size are operational. An economic utilization of this replenishable natural resource stands and falls with the economic feasibility of the extraction process, which until now has not been described, and which is made available for the first time by the present invention.

The present invention has, as a first objective, the provision of a process, which with the use of tenable solvents, makes possible the obtaining of large amounts of triterpenes with high purity in either the batch process or a continuous process. Besides this, this process should provide the possibility of utilizing the birch bark that is presently a waste product in the pulp industry. Besides this, the process should be simple, cost-effective, and rapidly completed. Further, it should be guaranteed that the amount of residual solvent in the extract falls within the guidelines of the European pharmaceutical handbook, and in particular, the "Guideline for Residual Solvents": ICH Q3C-Impurities (ICH=International Conference on Harmonization of technical requirements for registration of pharmaceuticals for human use). The present invention further addresses the task of providing a triterpene containing emulsion, which contains pharmaceutically active components, and at the same time, is sufficiently stable for a longer period of time without the addition of preservatives. Besides this, the emulsion should be capable of preparation in a simple manner.

The first task is solved, thereby, that in the inventive process for obtaining of triterpenes from plants and/or their components the plant parts are first washed at 20° C. to 70° C. in a solvent in which the triterpenes are not soluble or only slightly soluble.

Subsequently, the triterpenes are extracted with a solvent under increased pressure and elevated temperature. Next, there is carried out a cooling and simultaneous depressurization of the triterpene containing solution, whereby the triterpenes precipitate in the solvent in extremely small particles, and then, more triterpene crystallizes onto these particles upon further cooling. In order to further increase the purity of the triterpenes, they are washed following filtration at room temperature with a fresh solvent. By this process it is in particular achieved, that triterpenes can be obtained in simple manner on an industrial scale.

In the framework of the present invention, the expression "washing ( . . . ) in a solvent, in which the triterpene ( . . . ) is not or is only slightly soluble" means that the solubility of the triterpene is not more than 1 g/liter. By this first washing step, the easily soluble impurities are removed in an advantageous manner.

The extraction of the triterpene occurs with solvent under increased pressure and elevated temperature, in certain cases in the supercritical region. Therein, they can be used as solvents, for example, supercritical carbon dioxide, as well as hydrocarbons, in the supercritical region, as well as liquid hydrocarbons, under elevated pressure or mixtures of different hydrocarbons.

Prior to washing [step (e)], it is advantageous that it is not necessary to dry the filter cake in a further process step. Thereby, the process is particularly simple to carry out.

Besides this, the washing of the triterpene [step (e)] can itself be carried out under normal conditions, thereby keeping the inventive process particularly simple and economical.

Figure 1:
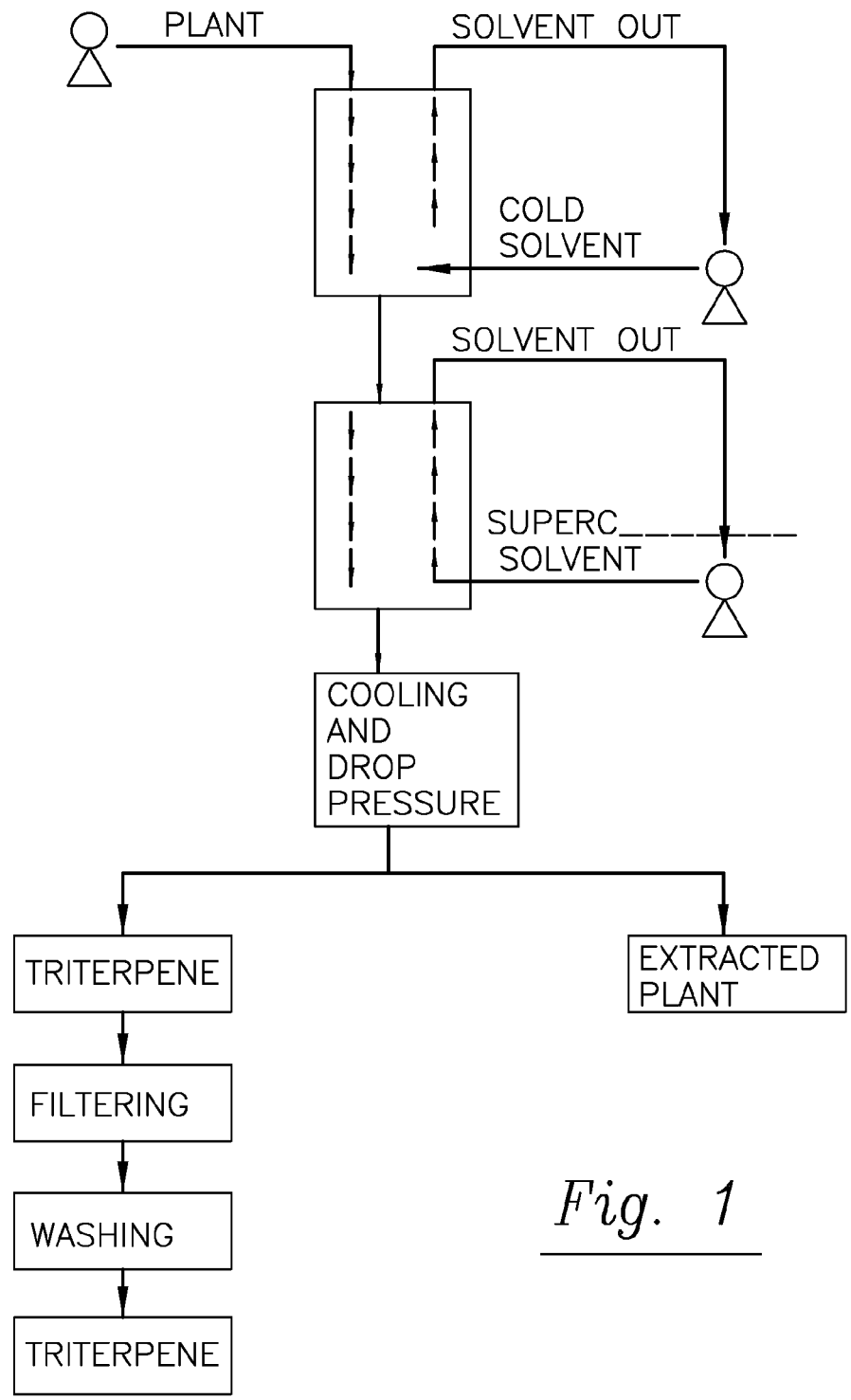
FIG. 1 shows the process according to the present invention.

In a particularly preferred embodiment, the inventive process is carried out continuously. For this, the plant material and cold solvent are conveyed through a pressure-tight tube by pumping, and washed in a counter-current at 20° C. to 70° C. By a second pump system, the washed plant material is conveyed in a second, likewise, pressure-tight and heatable tube, or pipe, and extracted in counter-current with fresh, supercritical heated or liquid solvent. The discharge of the wash solution and the extraction solution occurs, respectively, via a filter system. The plant parts are conveyed counter-current to the solvent flow, on the basis of their different density, and are discharged at the end opposite to the solvent discharge end. The extract solution is, with maintenance of the pressure in the extraction system, conveyed to spray nozzles via a valve system, and it is only here, that it is finally reduced in pressure.

Birch bark is available in large amounts as an economical raw material, in particular, as waste products in the pulp industry. In a preferred embodiment of the present invention, the triterpenes are obtained from birch bark, preferably from the white part of the birch bark, which is also referred to as birch cork.

"Separated birch cork" refers to both the white outer layer when stripped by hand, which is sloughed off outwardly, as cork skin by the trunk of the birches, and thus, lies outside of the actual bark, as well as the subsequently separated birch cork separated, for example, with the aid of a hammer mill and a flotation process from a total skinning.

In a particularly preferred embodiment, the triterpene is obtained in a purity of at least 80%, preferably 85%, in particular 90%, particularly preferably above 90%.

In a further illustrative embodiment, the main component of the extracted triterpene is betulin, wherein its content is at least 80%, preferably 85%, in particular 90%, particularly preferably above 90%.

Further, it is advantageous to use the same solvent for the first washing step, the actual extraction, and the subsequent washing step. In this manner, the best purity values can be achieved. Beyond this, it is particularly simple to carry out the process when using only one single solvent.

As solvent there is particularly suitable a low boiling hydrocarbons or a mixture, which includes a low boiling hydrocarbons, since a low boiling hydrocarbons can be subsequently very easily removed. The boiling point of the employed hydrocarbons, or, as the case may be, the mixture, preferably lies below 100° C. Particularly preferred is the employment of n-pentane, n-hexane or n-heptane, since all are inexpensive, do not harbor any special health hazards and are available in sufficient quantities in good quality.

It has been found to be of particular advantage to employ for the first washing step that solvent, which was collected as filtrate after the main extraction. In this manner, large amounts of impurities are removed from the starting material in advance, without having to expend any additional fresh solvent. These contaminations or impurities would have had a negative influence on the degree of purity following extraction. In order to further increase the degree of purity, the extracted components can be subsequently post washed with fresh solvent.

In a preferred embodiment, the first washing step is carried under a pressure of 1 to 300 bar, preferably 10 to 35 bar, particularly preferably about 25 bar. The actual extraction occurs preferably at a temperature of 50 to 200° C., preferably 140 to 160° C., particularly preferably about 150° C., and under a pressure of 1 to 300 bar, preferably 10 to 35 bar, particularly preferably about 25 bar. In these extraction conditions, large amounts of pure triterpenes, in particular pure betulin, are obtained.

The inventive process has also been found to be of particular advantage, when the crystallization of the triterpene occurs as micro-crystallization with an average particle size of <40 μm, in particular from 2 to 32 μm.

A further attribute of the present invention, is an emulsion, of which the aqueous and fatty phases are emulsified by a plant extract, wherein the plant extract includes at least one triterpene and/or at least one derivative of a triterpene, and the emulsion further includes at least one oil and/or fat and water.

The triterpene and/or its derivative, preserves and emulsifies the emulsion. Besides this, it is pharmaceutically active. Thereby, it is in particular achieved, that the emulsion contains no supplemental preservative, and thus, possesses a particularly high degree of purity and a good compatibility above all with problematic applications to damaged skin.

The plant extract is herein an extract of birch bark, preferably from the white part of the birch bark, which is referred to as birch cork.

In a further embodiment, the plant extract contains at least one of the substances betulin, betulinic acid, betulonic acid, lupeol (lupol), erythrodiol, allobetulin, phellonic acid, hydroxy-lactone, betulonic aldehyde, β-amyrin, oleanolic acid, ursolic acid, esterified betulin, and/or β-sitosterol. These plant constituents could be employed individually, as well as mixed with each other in various combinations in the inventive emulsion. A particularly suitable combination is comprised of betulin >80%, betulinic acid <10%, lupeol <3%, oleanolic acid <4%, erythrodiol <4% and water <1%.

The emulsion preferably contains the triterpene and/or its derivative in a concentration of 2 to 10%. Depending upon the desired consistency, the proportion of the triterpene and/or its derivative can be varied in the mentioned concentration range. For the employment of a fluid lotion, the emulsion exhibits, for example, a concentration of the triterpene and/or its derivative of 2 to 3.5%. If the emulsion is used in the form of a cream, the concentration of the triterpene and/or its derivative is preferably 3.5 and 10%.

The oily and/or fatty component of the emulsion can be selected from any of the dermatological and cosmetic known oils and fats. Particularly suitable are animal and plant fats, such as—jojoba oil, peanut oil, and olive oil. Particularly preferred is the use of avocado and/or almond oil.

In order to regulate the consistency of the inventive emulsion, conventional moisturizers and/or thickeners and solidifiers can be employed. As moisturizers glycerin and urea or carbamide can be employed. Herein above, all concentrations of, respectively, 3 to 10% glycerin and/or urea or carbamide are suitable, based upon the amount of the emulsion. As thickener there can be employed, for example—polysaccharides, which are to be added in a concentration of 0.2 to 2%, preferably 0.5%, based upon the amount of the employed water. Natural polysaccharides, as well as further sugar compounds, and their derivatives, are particularly suitable, since they do not react with the other components of the emulsion, they do not modify them, and are, thus, chemically inert.

Thus, the polysaccharide agar agar is preferably employed. Agar agar is a mixture of agarouse and agaropectin, which is obtained from red algae and has the advantage that it cannot be decomposed by most micro-organisms. Alternatively, the polysaccharide carrageenan can be employed, which occurs naturally in the cell wall of red algae and certain brown algae and has the same advantages as agar agar.

In a further embodiment, the emulsion comprises 2 to 10% extract from the white part of the birch bark, 20 to 30% avocado oil, 10 to 20% almond oil and 40 to 68% water. The most preferred concentrations comprise 4% extract from the white part of the birch bark, 29.3% avocado oil, 14.7% almond oil, and 52% water.

A further inventive emulsion contains 2 to 10% extract from the white part of the birch bark, 20 to 30% avocado oil, 10 to 20% almond oil, 5 to 10% moisturizing agent, and 30 to 63% water. Herein the most preferred is the concentration of 4% extract from the white part of the birch bark, 29.3% avocado oil, 14.7% almond oil, 5% glycerin and/or 5% urea, and 42 to 47% water.

The extract from the white part of the birch bark, which is contained in all emulsions, comprises at least 80% betulin, at most 10% betulinic acid, at most 3% lupeol and at most 4% oleanolic acid.

The emulsion, on the basis of its composition and its verifiable biocompatibility, is particularly suitable as a salve base for addition of all known fragrances, cosmetics, and medicinal active agents.

A further attribute of the invention is a process for producing the inventive emulsion, wherein the process includes the following steps:

(a) dispersion of triterpene in an oil and/or fat;
(b) emulsification of water;
(c) homogenization of the emulsion to the desired consistency.

Herein, the dispersion and homogenization preferably occurs in a homogenizing mixer, since the process can be carried in particularly simple manner in this way. Further, it is possible to prepare small amounts of emulsion for individual applications.

In a particularly preferred embodiment, there is added to the water, which is used during emulsification, a moisturizing agent, in particular glycerin and/or urea, or a thickener, in particular a polysaccharide. Thereby, a particularly creamy consistency can be achieved.

A further attribute of the present invention is the use of the triterpenes for manufacture of a cosmetic, preferably in the form of a salve, a lotion, a cream, a gel, a jelly, a tincture, a shampoo, a powder and/or a cosmetic (compact) powder, in particular for application upon the skin, the face or scalp or scalp and/or for inhalation. On the basis of its chemical relationship to sterols the triterpenes, in particular the obtained betulin, are particularly suitable for skin and head care. It relaxes and smoothes skin, reduces the water loss and induces attractiveness and blush. Thereby, the cosmetic can be particularly employed for maintaining moisture of the skin and smoothing the skin, as well as for reduction of age spots and can be employed in the case of dandruff or flaking skin. A further advantage is the water insolubility of the triterpenes, so that skin, which is exposed to water vigorously and for prolonged periods, is particularly well protected. On the basis of the anti-bacterial effect, the use as deodorant is particularly advantageous. Added to this is the minimization of transpiration on the basis of an effective closure of the sweat glands.

A further attribute of the present invention is the use of the triterpenes for production of a pharmaceutical or medicinal formulation, preferably in the form of a salve, a lotion, a cream, a gel, a jelly, a tincture, a shampoo, a powder and/or a cosmetic (compact) powder, in particular for application upon the skin, the face or scalp or scalp, and/or for inhalation, particularly preferably for treatment of dermatological conditions of the skin and/or the scalp, above all, for neurodermitis, psoriasis, contact eczema, melanoderma, impetigo, pre-cancerous conditions of the skin, as well as for inhalation during asthmatic attacks and/or for substitution in place of glucocorticoids. Likewise, on the basis of their high purity, the obtained triterpenes, in particular the obtained betulin, is suitable for the therapeutic application on pre-cancerous skin.

The inventive emulsion is so well-suited for the above-mentioned applications because the extract from the white part of the birch bark includes no mutagenic characteristics. Topical toxicity tests were likewise carried out, wherefrom no sensitizing characteristics were discovered.

The following examples serve for illustrating and imparting a better understanding of the present invention, but should in no way be considered as limitations.

EXAMPLES

I. Clinical Observations

Various clinic observations of dermatological skin changes were carried out by general practice doctors, as well as clinical doctors. Following the diagnosis by the doctors, there occurred, a treatment of the patients with the inventive emulsion, which was produced in accordance with described processes.

Example 1

| | |
|---|---|
| Patient: | male, 68 years |
| Diagnosis: | heavy, generalized psoriasis vulgaris |
| Pre-Treatment: | medium strength cortisone salve |
| Application: | scalp |
| Treatment: | multiple daily application of the inventive emulsion as salve upon the afflicted skin areas |
| Results: | the occurrence of psoriasis efflorescence following application of the cortisone salve was prevented by the application of the inventive emulsion |

Example 2

| | |
|---|---|
| Patient: | male, 48 years |
| Diagnosis: | light psoriasis vulgaris |
| Pre-Treatment: | medium strength cortisone salve |
| Application: | head |
| Treatment: | multiple daily application of the inventive emulsion as salve upon the afflicted skin areas |
| Results: | healing of the approximately dollar-piece sized presternal inflamed focal areas of the infection on the head upon application of the inventive emulsion within 14 days; re-inflammation of the infection (=recidivist) after cessation of application of emulsion; renewed definite improvement upon resumption of the treatment |

Example 3

| | |
|---|---|
| Patient: | female, 5 months |
| Diagnosis: | neurodermitis, hyperkeratotic, prematurely aged, chapped-shriveled skin |
| Application: | body |
| Treatment: | multiple daily applications of the inventive emulsion as salve upon the afflicted skin areas |
| Results: | very noticeable improvement, excellent effectiveness with simultaneously good compatibility |

Example 4

| | |
|---|---|
| Patient: | female, 10 years |
| Diagnosis: | neurodermitis, hyperkeratotic, prematurely aged, chapped-shriveled skin |
| Application: | body |
| Treatment: | multiple daily applications of the inventive emulsion as salve upon the afflicted skin areas |
| Results: | very noticeable improvement, excellent effectiveness with simultaneously good compatibility |

Example 5

| | |
|---|---|
| Patient: | male, 5 months |
| Diagnosis: | neurodermitis, hyperkeratotic, prematurely aged, chapped-shriveled skin |
| Application: | body |
| Treatment: | multiple daily applications of the inventive emulsion as salve upon the afflicted skin areas |
| Results: | very noticeable improvement, excellent effectiveness with simultaneously good compatibility. |

Example 6

| | |
|---|---|
| Patient: | female, 28 years |
| Diagnosis: | neurodermitis, neuodermitic effloresce |
| Application: | elbows, face or scalp, neck line |
| Pre-Treatment: | Dermatodoron, Stibium metallicum salve, Top-isolon-bartel salve, mesembryanthemum salve, following application of these salves, there resulted no overall improvement of the neurodermitic sites |
| Treatment: | multiple daily application of the inventive emulsion as salve upon the afflicted skin areas |
| Results: | significant reduction of the neurodermitis |

Example 7

| | |
|---|---|
| Patient: | female, 78 years |
| Diagnosis: | seborrheic eczema |
| Application: | head |
| Treatment: | multiple daily application of the inventive emulsion as salve upon the afflicted skin areas |
| Results: | reduction of scab formation in the scalp area, red areas blistered somewhat slower |

Example 8

| | |
|---|---|
| Patient: | female, 55 years |
| Diagnosis: | strong itching, dandruff, moist eczema |
| Application: | scalp, head |

-continued

| Treatment: | multiple daily application of the inventive emulsion as salve upon the afflicted skin areas |
| --- | --- |
| Results: | visible improvement of the treated areas |

Example 9

| Patient: | female, 33 years |
| --- | --- |
| Diagnosis: | dry, itching, easily infected scabbing eczema |
| Application: | lower side |
| Treatment: | multiple daily application of the inventive emulsion as salve upon the afflicted skin areas |
| Results: | not yet evaluated |

II. Production of the Plant Extract
  Starting Material: Birch cork
  A) Description of Quality Assurance
  The birch cork was delivered by:
1. The "wood pulp company Kaukas" (UPM-Kymmene Lappeenranta, Finland).

Kaukas separates the bark mechanically from the birch wood, and the cork is also mechanically removed from the inner bark.
2. Co-workers, which cut the cork by hand.
  In a first step, the mechanically separated and the hand cut cork is analyzed regarding its identity. For this purpose, the cork is microscopically examined, whereby multiple individual cork layers and lenticular cells, which are typical for birch, can be seen. In addition, the extractable amount of triterpenes with n-hexane at 140 to 160° C. under increasing pressure is examined. The extractable amount of triterpene with the main component betulin exceeded 10%, since such amounts occur only in the cork of birches with white bark. For the monitoring of purity of the material, subsequently an analysis with respect to aflatoxins, heavy metals, herbicides and pesticides was carried out according to European standards.

B) Shredded Cork
  The cork was ground in a cutting mill (produced by the company Retsch) and suctioned off out of the machine through a sieve with a pore size of 1 mm diameter.
  For the further extraction, only particles with a particle size ≦1 mm were employed.

Extraction of the Triterpene:
  For extraction, advantage was taken of the phenomenon that triterpene is practically insoluble from birch cork in cold n-hexane is, however, well-soluble in hot n-hexane (140 to 160° C.) under pressure. This process was carried out in two steps:

1. The cork was cleansed in a Soxhlett apparatus, using a Soxhlett process with n-hexane (hot, <boiling point 69° C.), until the n-hexane solution was no longer yellow.
2. The active component or ingredient was extracted from the pre-washed cork granulate with n-hexane at 140 to 160° C. under elevated pressure (extraction by means of Dionex ASE 300 with 100 ml vessels). Upon the quenching of the overheated solution containing n-hexane and triterpene, a crystallization occurred immediately, so that a micro-crystalline powder of triterpene was obtained directly in the cold n-hexane. This powder was filtered and washed twice in cold n-hexane. The triterpene was dried at 80 to 100° C.

Determination of the Purity of the Extract:
  The purity of the extract was monitored using gas chromatography (GC). The result is represented in the following diagram.
    Overview: GC of the Extract of Birch Cork with Cholesterol as Internal Standard
  Determination: Active Substances in Salve
  Determination in Salve 018701

| Injection Date: | 14.01.01 02:37:52 | Seq. Line: | 20 |
| --- | --- | --- | --- |
| Sample Name: | W 7.1_salve 010701 containing Bd.013 | Location: | Vial 41 |
| Acq. Operator: | Beffert/Jäger | Inj: | 1 |
| Acq. Method: | C:\HPCHEM\2\METHODS\EU-UPM33.M | Inj. Volume: | 1 µl |
| Last changed: | 13.01.01 14:53:38 by Beffert/Jäger | | |
| Analysis Method: | C:\HPCHEM\2\METHODS\EU-UPM33.M | | |
| Last change: | 14.01.01 10:44:27 by Beffert/Jäger (modified after loading) | | |
| Betulin Method of UPM - modified | | | |

The following values were measured:

| Betulin: | at least 80% |
| --- | --- |
| Betulinic acid: | at most 10% |
| Lupeol: | at most 3% |
| Oleanolic acid: | at most 4% |

The overview shows a typical gas chromatogram with values of 84 to 86% betulin, 4 to 5% betulinic acid, approximately 1% lupeol and approximately 1% oleanolic acid.

According to the requirements of the ICH, the amount of the solvent n-hexane remaining must be <7,725 mg/kg extract, while a cream containing 4% birch cork extract may not contain more than 290 mg/kg n-hexane. Typical values comprise 1,500 mg/kg n-hexane in dried extract, which corresponds to approximately 60 mg/kg in the birch cream.

Final Inspection:
  Each charge was checked according to the European requirements with respect to the acid value (<5) and the peroxide number (<15), by means of a standardized process. The content of birch cork extract was analyzed using GC. Further, an examination was made regarding microbes (<100/g); besides this, no pathological microbes may be contained.

III. Inventive Formulation (Birch Cream):

The inventive formulation is set forth in Table 1 (Tab. 1). They were comprised of the following composition:

TABLE 1

Composition of the Formulation

| Active Component in all Formulations | Extract from Birch cork 40 ± 4 mg/g Cream (4%) |
|---|---|
| Formulation | Ingredient in % |
| Birch Cream A | 29.3 Avocado oil |
|  | 14.7 Almond oil |
|  | 52 Water |
| Birch Cream G | 29.3 Avocado oil |
|  | 14.7 Almond oil |
|  | 5 Glycerin |
|  | 47 Water |
| Birch Cream H | 29.3 Avocado oil |
|  | 14.7 Almond oil |
|  | 5 Urea |
|  | 47 Water |

All three formations contained the same amount of the active component (birch cork extract), as well as avocado and almond oil. They differed, essentially, with respect to the component urea (only in birch cream H), as well as glycerin (only in birch cream G), birch cream A is free of these components.

Stability Test:

The birch cream was centrifuged at 500×g and was found to be stable therein.

IV. Toxicological Tests:

1. Acute toxicity

The acute toxicity of the birch cork extract was determined by intra-peritoneal and subcutaneous administration to mice and rats.

Mice:

Individual doses of birch cork extract (charge number: Bet. 001) in Methocel as carrier were subcutaneously administered to five male and five female CD-1 mice. The animals were treated with a dose of 2000 mg/kg, based upon their body weight.

The lethality was determined 14 days after the administration of an individual dose for determination of the average lethal dose $LD_{50}$. At the same time, the animals were observed in order to detect symptoms of toxicity. As such, there were considered local and systemic intolerance reactions, as well as changes in the body weight. The animals were sacrificed at the end of the experiment and examined microscopically. The acute toxicity test followed EC guidelines L 383 A: B1.

Under the given test conditions (2000 mg birch cork extract/kg body weight) no intolerance reactions were observed. The animals showed the expected weight gain during the experimental period. The results are assembled in Table 2 (Tab. 2).

TABLE 2

Acute Toxicity in Mice
Average body weight during the experimental period

| | Average Body Weight (g) | |
|---|---|---|
| | Male | Female |
| Beginning | 22.8 | 19.8 |
| Day 7 | 27.0 | 22.2 |
| Day 14 | 31.2 | 23.6 |

In the macroscopic examination, changes were observed in three males and three female animals, which could be traced back to the technical examination process employed.

In this toxicity test, the area of the first intolerance reaction, the lowest lethal value, as well as the $LD_{50}$ value, lies above 2000 mg birch cork extract/kg body weight.

Upon intra-peritoneal administration of the birch cork extract in mice, toxic symptoms were observed above 500 mg/kg body weight. Only light toxic reactions, such as reduced passive amount of movement, interference in movement coordination and reduced muscle stretch resistance were observed. From this it was concluded, that the toxic symptoms were to be traced back to stomach fur inflammation (peritonitis), which was brought about by the extract solution. A $LD_{50}$ value could not be determined, so that in the observed time period of 14 days this lies above 200 mg/kg body weight.

Rats:

Individual doses of birch cork extract (charge number: Bet. 001) in Methocel as carrier, were subcutaneously administered to five male and five female Sprague-Dawley rats. The animals were treated with a dose of 2000 mg/kg, based upon their body weight.

The lethality and toxic symptoms were determined 14 days after the administration of an individual dose. The animals were sacrificed at the end of the experiment and examined microscopically. The acute toxicity test followed EC guidelines L 383 A: B 1.

Under the given test conditions (2000 mg birch cork extract/kg body weight), no intolerance reactions or lethality were observed. The animals showed the expected weight gain during the experimental period.

In the macroscopic examination, changes were observed in three males and three female animals, which could be traced back to the technical examination process employed. The results are assembled in Table 3 (Tab. 3).

TABLE 3

Acute Toxicity in Rats

| | Sprague-Dawley Rats (n = 5/sex) Birch cork extract 2000 mg/kg body weight | |
|---|---|---|
| Symptoms/Criteria | Male | Female |
| Local intolerance reaction | none | none |
| Systemic intolerance reaction | small | small |
| Mortality within 6/24 hours in 7/14 days | none | none |
| Average body weight (g) | | |
| Beginning | 187.6 | 174.4 |
| Day 7 | 239.8 | 203.8 |
| Day 14 | 280.8 | 218.0 |

TABLE 3-continued

Acute Toxicity in Rats

| | Sprague-Dawley Rats (n = 5/sex) Birch cork extract 2000 mg/kg body weight | |
| --- | --- | --- |
| Symptoms/Criteria | Male | Female |
| Loss of body weight | none | none |
| Macroscopic result | 1/5 | 3/5 |

In this toxicity test the range of the first intolerance reaction, the lowest lethal value, as well as the $LD_{50}$ value, lies above 2000 mg birch cork extract/kg body weight.

Upon intra-peritoneal administration of the birch cork extract in rats, toxic symptoms were observed above 500 mg/kg body weight. Only light toxic reactions, such as reduced passive amount of movement, interference in movement coordination and reduced muscle stretch resistance were observed. From this it was concluded, that the toxic symptoms were to be traced back to stomach fur inflammation (peritonitis), which was brought about by the extract solution. A $LD_{50}$ value could not be determined, so that in the observed time period of 14 days this lies above 200 mg/kg body weight.

Further Actions:

The OECD guidelines establish that no further experimentation is necessary, when over a time span of 14 days with an administration of 2000 mg/kg body weight in mice and rats (for each five animals/sex), no mortality resulted from the tested product.

Chemicals are classified on the basis of their relative toxicity. They are characterized as toxic when the $LD_{50}$ valve lies between 50 and 500 mg/kg body weight. With a $LD_{50}$ value of 5000 to 15000 mg/kg body weight, there is the presumption of practically no toxicity.

In the present case, it has been established that the $LD_{50}$ value is >2000 mg/kg body weight, and is very likely also >5000 mg/kg body weight, since even with the high value of 2000 mg/kg body weight, no toxic symptoms were observed. As can be seen from the experimental results, the birch cork extract can be characterized as non-toxic.

2. Sub-acute Toxicity

Rats, Intra-Peritoneal (i.p.)

Birch cork extract (charge-number: Bet. 009) was administered to experimental rats (Sprague-Dawley/Crl: CD® BR) by means of intra-peritoneal injection over 14 days within the framework of a sub-acute toxicity test. The test protocol is summarized in Table 4 (Tab. 4).

TABLE 4

Test Protocol of a Sub-acute Toxicity Test (Rats, i.p.)

Animals:

40: (20 male, 20 female) Sprague-Dawley Crl: CD ® BR rats
Animal Groups:

Group 1-5
5 male/5 female animals in each group
Additional 4 (2 male, 2 female) reserve animals, as possible replacements during the acclimation phase
Test Protocol*:

Birch cork extract
(=component of birch cream)
Batch number: Bet. 009
Carrier: sesame oil
Dose Amount:

Group 1: 20 ml carrier/kg body weight/day
Group 2: 500 mg/kg body weight/day
Group 3: 1000 mg/kg body weight/day
Group 4: 2000 mg/kg body weight/day
Administration Volume:

20 ml/kg body weight/day
Number of Doses: 1
Administration Period:

14 days (day 1-14)
Test Period:

15 days (day 1-15)

*the triterpene in the birch extract is insoluble in the carrier and exists as homogeneously distributed particles (micro-crystalline powder)

This sub-acute toxicity test was used for determining the dose, which was employed in a four week sub-chronic toxicity test. The results of the toxicity test are shown in Table 5 (Tab. 5).

TABLE 5

| | Sub-acute Toxicity Tests in Rats | | | |
| --- | --- | --- | --- | --- |
| | 1 | 2 | 3 | 4 |
| Mortality | none | none | none | N = 8[1] |
| Clinical Result: greatly enlarged abdomen | none | in individual[2] animals >Day 13 | >Day 10 | in all animals >Day 7 |
| Raw fur | none | none | >Day 10 | in all animals >Day 7 |

TABLE 5-continued

Sub-acute Toxicity Tests in Rats

| | 1 | 2 | 3 | 4 |
|---|---|---|---|---|
| Lose in body Weight | none | −18%* −15% | in all male animals >week 1: −14%* End of week 2: −12% | in both sexes >Week 1: −15%* (male) −12% (female) |
| Change in food Intake | none | none | none | reduction in test week 1: male: −29% female: −31% |
| Hemotological Change | none (see Tab. 6) | none see (Tab. 6) | differences to the control group (see Tab. 6) | |
| Changes in Clinical Biochemistry | none (see Tab. 6) | Urea ASAT (see Tab. 6) | Urea ASAT LDH (see Tab. 6) | Urea ASAT LDH and all further parameters in the female animals and almost all further parameters in the male animals |

Explanations for Tab. 5:
*p ≦ 0.01 in comparison to the control group
[1] 4 male, 4 female animals (Days 11-15)
[2] 4 of 5 females, 2 of 5 male animals The changes in the clinical biochemistry (Tab. 5) are significant relative to the control only in groups 3 and 4 (p≦0.01); in Group 3 with respect to the ASAT activity (+113/+132%), in Group 4 only with female animals with respect to the parameters: total protein, urea in the blood, calcium, potassium, and LDH activity.

TABLE 6

Hematological changes in the sub-acute toxicity test (Rat, i.p.) - Definition of Groups 3 and 4 in comparison to Tab. 5

| | Group | | | |
|---|---|---|---|---|
| | 3 changes in % | | 4 changes in % | |
| Parameter | male | female | male | female |
| platelet count | — | +47** | +80 | +54** |
| Reticulocyte count | — | — | +64 | +36** |
| Leukocyte count | — | — | — | −34 |

Explanation for Tab. 6:
**p ≦ 0.01 in comparison to the control group.

The external examination prior to the necroscopic examination, showed a significant to heavy enlargement of the abdomen in all groups, with the exception of the control group, in which the abdomen in all animals was only slightly enlarged. The results of the macroscopic post-mortem examination are shown in Table 7 (Tab. 7).

TABLE 7

Necroscopic result in the sub-acute toxicity test - Definition of the Groups in comparison to Tab. 4

| | Group | | | |
|---|---|---|---|---|
| | 1 | 2 | 3 | 4 |
| White yellow fluid in abdominal cavity[1] | + | + | + | + |
| White deposit or layer upon the diaphragm or upon the abdominal organs | none | + | + | + |
| Stomach fur inflammation | none | none | none | + |
| Abdominal space filled with white pulp-like/oily content | none | none | none | +approximately 30 ml |

Explanation for Tab. 7:
[1] in 4 animals

In this two week test for determination of the dose amount, the amount without effect lies at <500 mg birch extract/kg body weight. Significantly strong enlargement of the abdomen was observed at 500 mg/kg body weight and higher. Significant reduction of body weight was observed in all treated groups, however, only in the male animals. Coarse or inflamed fur was observed at 1000 mg/kg body weight and higher. Certain hematological and/or biochemical parameters were changed significantly at 1000 mg/kg body weight and higher. The necroscopic examination showed white deposits upon the diaphragm or the abdominal organs, which were partially accompanied by adhesions at 500 mg/kg body weight and higher. In all groups, the abdominal cavity was filled with an oily/watery fluid, which could be traced back to the carrier sesame oil. At 2000 mg/kg body weight 8 of 10 animals died. The necroscopic examination showed: 1) stomach fur infection in 4 of the prematurely deceased animals; and 2) in all animals the abdominal cavity was filled with pulp-like/oily content. For the sub-chronic toxicity test an amount of 60 to 540 mg/kg body weight was selected.

Dogs (Beagle), i.p.

A sub-acute toxicity was carried out over a period of two weeks with Beagles, as dose-determining experiment, over four weeks, as sub-chronic toxicity test. The birch cork extract (Batch No.: Bet. 009) was administered intra-peritoneal with sesame oil as the carrier. The results are summarized in Table 8 (Tab. 8).

TABLE 8

Sub-acute toxicity test in dogs (Beagle), i.p.
Dose amount:

1. MTD* time
   50, 150, 250, 500 mg/kg body weight/day
2. Fixed dose time
   100, 300 mg/kg body weight/day Animals: 8 Beagles
2 beagles per sex and group
Explanation for Tab. 8:
*MTD: maximal tolerance dose The results are shown in Table 9 (Tab. 9).

TABLE 9

Sub-acute toxicity test in dogs (beagles), i.p.

No effect:

<50 mg/kg body weight/day during the MTD time
Lethal dose:

500 mg/kg body weight/day
Toxic indication during the fixed dose time:

(100, 300 mg/kg body weight/day)
Reduced body weight
Reduced food uptake
Change in hematopoetic and biochemical parameters
Heavy stomach fur inflammation in 3 of 8 animals*

Explanation for Tab. 9:
*These animals were killed one week after the last dose on the basis of their poor condition.

The invention claimed is:

1. An emulsion, comprising:
an aqueous phase;
a fatty phase; and
water;
wherein the aqueous phase and the fatty phase are emulsified using a plant extract,
wherein the plant extract is at least one triterpene, or at least one derivate of a triterpene;
wherein the fatty phase contains at least one oil and/or fat;
wherein the triterpene and/or its derivative is the only emulsifier and preservative in the emulsion;
wherein the proportion of triterpene and/or its derivative comprises 2 to 10% of the total weight of the emulsion.

2. The emulsion according to claim 1, wherein the plant extract is a birch bark extract.

3. The emulsion according to claim 2, wherein the emulsion comprises 2 to 10% birch bark extract, 20 to 30% avocado oil, 10 to 20% almond oil, 5 to 10% moisturizing agent and 30 to 63% water.

4. An emulsion according to claim 3, wherein the emulsion comprises 4% birch bark extract, 29.3% avocado oil, 14.7% almond oil, 5% glycerin and/or 5% urea and from 42 to 47% water.

5. The emulsion according to claim 1, wherein the emulsion further includes at least one moisturizing agent and/or at least one thickening agent.

6. The emulsion according to claim 5, wherein the thickening agent is a polysaccharide, which is added in a concentration of 0.2 to 2%, preferably 0.5%, based upon the amount of water.

7. The emulsion according to claim 6, wherein the polysaccharide is agar agar or carrageenan.

8. The emulsion according to claim 5, wherein the moisturizing agent is glycerin and/or urea, which is added in a concentration of 3 to 10%, preferably 5% of each, based upon the amount of the emulsion.

9. The emulsion according to claim 1, wherein the triterpene comprises betulin and, optionally, is at least one substance selected from the group consisting of betulinic acid, lupeol, erythrodiol, allobetulin, phellonic acid, hydroxy-lactone, betulin aldyhyde, β-amyrin, oleanolic acid, ursolic acid, esterified betulin and/or β-sitosteol.

10. The emulsion according to claim 1, thereby characterized, that the proportion of triterpene and/or it derivative comprises 2 to 3.5% or 3.5 to 10% of the total weight of the emulsion.

11. An emulsion according to claim 1, wherein the plant extract comprises at least 80% betulin, at most 10% betulinic acid, at most 3% lupeol and at most 4% oleanolic acid.

12. An emulsion, comprising:
an aqueous phase;
a fatty phase; and
water;
wherein the aqueous phase and the fatty phase are emulsified using a plant extract,
wherein the plant extract is at least one triterpene, or at least one derivate of a triterpene;
wherein the fatty phase contains at least one oil and/or fat;
said emulsion excluding any emulsifier other than the triterpene and/or it derivative; and wherein the emulsion includes 2 to 10% plant extract, 20 to 30% avocado oil, 10 to 20% almond oil and 40 to 68% water.

13. The emulsion according to claim 12, wherein the emulsion comprises 4% plant extract, 29.3% avocado oil, 14.7% almond oil and 52% water.

14. An emulsion comprising:
an aqueous phase;
a fatty phase; and
water;
wherein the aqueous phase and the fatty phase are emulsified using a plant extract,
wherein the plant extract is at least one triterpene or at least one derivate of a triterpene;
wherein said emulsion includes a preservative, an emulsifier and an pharmaceutical active substance;
said preservative consisting of the triterpene or at least one derivate of a triterpene;
said emulsifier consisting of the triterpene or at least one derivate of a triterpene;
said active substance consisting of the triterpene or at least one derivate of a triterpene, said emulsion excluding any emulsifier other than the triterpene and/or a derivative thereof; and wherein the proportion of triterpene and/or its derivative comprises approximately 2% to approximately 10% of the total weight of the emulsion.

15. An emulsion, comprising:
an aqueous phase;
a fatty phase; and
water;
wherein the aqueous phase and the fatty phase are emulsified using a plant extract,
wherein the plant extract is at least one triterpene, or at least one derivate of a triterpene;
wherein the fatty phase contains at least one oil and/or fat;
wherein the triterpene and/or its derivative is the only emulsifier and preservative in the emulsion;
wherein the emulsion further includes at least one moisturizing agent;

and wherein the moisturizing agent is glycerin and/or urea, which is added in a concentration of 3 to 10%, preferably 5% of each, based upon the amount of the emulsion.

16. The emulsion according to claim 15, wherein the proportion of triterpene and/or its derivative comprises 2 to 10% of the total weight of the emulsion.

17. An emulsion, comprising:
an aqueous phase;
a fatty phase; and
water;
wherein the aqueous phase and the fatty phase are emulsified using a plant extract,
wherein the plant extract is at least one triterpene, or at least one derivate of a triterpene;
wherein the fatty phase contains at least one oil and/or fat;
wherein the triterpene and/or its derivative is the only emulsifier and preservative in the emulsion;
wherein the emulsion further includes at least one thickening agent; and
wherein the thickening agent is a polysaccharide, which is added in a concentration of 0.2 to 2%, preferably 0.5%, based upon the amount of water.

18. The emulsion according to claim 17, wherein the proportion of triterpene and/or its derivative comprises 2 to 10% of the total weight of the emulsion.

* * * * *